United States Patent
Aragaki

(10) Patent No.: US 11,181,463 B2
(45) Date of Patent: Nov. 23, 2021

(54) IMAGE PROCESSING DEVICE, CELL RECOGNITION APPARATUS, CELL RECOGNITION METHOD, AND CELL RECOGNITION PROGRAM

(71) Applicant: OLYMPUS CORPORATION, Hachioji (JP)

(72) Inventor: Hideya Aragaki, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 294 days.

(21) Appl. No.: 16/435,227

(22) Filed: Jun. 7, 2019

(65) Prior Publication Data

US 2019/0383724 A1 Dec. 19, 2019

(30) Foreign Application Priority Data

Jun. 14, 2018 (JP) .............................. JP2018-113230

(51) Int. Cl.
*G01N 15/14* (2006.01)
*G16H 30/40* (2018.01)
*G06T 7/00* (2017.01)

(52) U.S. Cl.
CPC ....... *G01N 15/1434* (2013.01); *G06T 7/0012* (2013.01); *G16H 30/40* (2018.01); *G01N 2015/1445* (2013.01); *G01N 2015/1493* (2013.01)

(58) Field of Classification Search
None
See application file for complete search history.

(56) References Cited

U.S. PATENT DOCUMENTS

2011/0130653 A1* 6/2011 Wang .................. G06T 7/70
600/425

FOREIGN PATENT DOCUMENTS

WO 2005057496 A1 6/2005

OTHER PUBLICATIONS

WO2005057496 Ito et al, wipo-english; https://patentscope.wipo.int/search/en/detail.jsf?docId=JP271092540&tab=FULLTEXT&_cid=P 11-KKJ777-39385-1 (Year: 2005).*

* cited by examiner

Primary Examiner — Jianxun Yang
(74) Attorney, Agent, or Firm — Holtz, Holtz & Volek PC

(57) ABSTRACT

An image processing device includes a processor configured to: set a plurality of first seed positions, pixel values of which indicate three-dimensional peaks, in a stack image of a cell; give an identification number to each first seed position; set a standard size of a cell in a predetermined direction of the stack image; set, referring to each first seed position, second seed positions within a range of the standard size centering on each first seed position, the second seed positions being positions shifted in the predetermined direction with respect to the first seed positions; give the same identification number as the identification number of the first seed position of a reference source to each second seed position; and form two-dimensional cell regions in all the first seed positions and thereafter form two-dimensional cell regions in the second seed positions.

20 Claims, 14 Drawing Sheets

IMAGE PROCESSING DEVICE, CELL RECOGNITION APPARATUS, CELL RECOGNITION METHOD, AND CELL RECOGNITION PROGRAM

CROSS-REFERENCE TO RELATED APPLICATIONS

This application claims the benefit of Japanese Patent Application No. 2018-113230, the content of which is incorporated herein by reference.

TECHNICAL FIELD

The present invention relates to an image processing device, a cell recognition apparatus, a cell recognition method, and a cell recognition program.

BACKGROUND ART

Various cell analyses using cell images photographed through a microscope have been performed in the medical/life science field. For example, in researches of stem cells such as ES cells and iPS cells, work for observing differentiation processes and morphological characteristic changes of cells are observed from a plurality of cell images photographed in time series and examining differences in characteristics of each of the cells has been generally performed for the purpose of elucidation of a cell differentiation mechanism, drug discovery and development, and the like. Concerning an analysis of a cell image, by applying an image analysis technique such as image recognition, it is becoming possible to automate complicated work such as screening of individual cells that is visually performed in the past.

Further, for the purpose of, for example, examining effects of medicines and the like in an environment closer to an in vivo environment, it is becoming possible to perform three-dimensional culture for stereoscopically cultivating cells and three-dimensionally analyze a culture state of a cell conglomerate, which is a stereoscopic aggregation of a plurality of cells, by applying the image analysis technique. If such an image analysis technique is applied, it is possible to efficiently grasp morphological information, the number of individuals, and the like of cells by automatically detecting individual cells included in a cell image.

PTL 1 discloses a method of detecting an object in a two-dimensional or three-dimensional image. Specifically, in PTL 1, a feature value of a predetermined region including a pixel of attention is calculated based on a pixel value of the predetermined region, the feature value of the predetermined region is set as a score of the pixel of attention, pixels are selected in descending order of the scores, exclusive regions same as or approximate to the predetermined region are disposed in positions of the selected pixels, and at least a part of finally disposed exclusive regions is detected as an object.

For example, in an image of a cell, a pixel value of a core region is larger than a pixel value of a background. Therefore, scores including a peak score in the core region are used and circular or spherical exclusive regions are disposed in order from a pixel having the largest score, whereby a position of a cell, which is an object, is specified.

CITATION LIST

Patent Literature

{PTL 1} PCT International Publication No. WO 2005/057496

SUMMARY OF INVENTION

One aspect of the present invention is an image processing device that forms a three-dimensional cell region from a stack image obtained by photographing a plurality of cells, the stack image being configured from a plurality of two-dimensional slice images stacked in a stack direction, the three-dimensional cell region being formed by stacking a plurality of two-dimensional cell regions, the image processing device including a processor configured to: set a plurality of first seed positions in the stack image, each of the plurality of first seed positions being a position of a pixel, a pixel value of which indicates a three-dimensional peak; give a unique identification number to each of the plurality of first seed positions; set a standard size of a cell in a predetermined direction of the stack image; set, referring to each of the plurality of first seed positions, second seed positions within a range of the standard size centering on each of the plurality of first seed positions, the second seed positions being positions shifted in the predetermined direction with respect to the first seed positions; give an identification number to each of the second seed positions, the identification number of each of the second seed positions being same as the identification number of the first seed position referred to in the setting of the second seed positions; and form a two-dimensional cell region in each of the first and second seed positions, the two-dimensional cell region being a region crossing the predetermined direction, wherein in the forming of the two-dimensional cell region, the processor is configured to form the two-dimensional cell region in each of all the first seed positions and thereafter form the two-dimensional cell region in each of the second seed positions.

Another aspect of the present invention is a cell recognition method for forming a three-dimensional cell region from a stack image obtained by photographing a plurality of cells, the stack image being configured from a plurality of two-dimensional slice images stacked in a stack direction, the three-dimensional cell region being formed by stacking a plurality of two-dimensional cell regions, the image recognition method including: setting a plurality of first seed positions in the stack image, each of the plurality of first seed positions being a position of a pixel, a pixel value of which indicates a three-dimensional peak; giving a unique identification number to each of the plurality of first seed positions; setting a standard size of a cell in a predetermined direction of the stack image; setting, referring to each of the plurality of first seed positions, second seed positions within a range of the standard size centering on each of the plurality of first seed positions, the second seed positions being positions shifted in the predetermined direction with respect to the first seed positions; giving an identification number to each of the second seed positions, the identification number of each of the second seed positions being same as the identification number of the first seed position referred to in the setting of the second seed positions; and forming a two-dimensional cell region in each of the first and second seed positions, the two-dimensional cell region being a region crossing the predetermined direction, wherein in the forming of the two-dimensional cell region, the two-dimensional cell region is formed in each of all the first seed positions and thereafter the two-dimensional cell region is formed in each of the second seed positions.

Another aspect of the present invention is a non-transitory computer-readable medium having a cell recognition program stored therein, the cell recognition program causing a processor to execute processing for forming a three-dimensional cell region from a stack image obtained by photographing a plurality of cells, the stack image being configured from a plurality of two-dimensional slice images stacked in a stack direction, the three-dimensional cell region being formed by stacking a plurality of two-dimensional cell regions, the cell recognition program causing the processor to execute functions of: setting a plurality of first seed positions in the stack image, each of the plurality of first seed positions being a position of a pixel, a pixel value of which indicates a three-dimensional peak; giving a unique identification number to each of the plurality of first seed positions; setting a standard size of a cell in a predetermined direction of the stack image; setting, referring to each of the plurality of first seed positions, second seed positions within a range of the standard size centering on each of the plurality of first seed positions, the second seed positions being positions shifted in the predetermined direction with respect to the first seed positions; giving an identification number to each of the second seed positions, the identification number of each of the second seed positions being same as the identification number of the first seed position referred to in the setting of the second seed positions; and forming a two-dimensional cell region in each of the first and second seed positions, the two-dimensional cell region being a region crossing the predetermined direction, wherein in the forming of the two-dimensional cell region, the two-dimensional cell region is formed in each of all the first seed positions and thereafter the two-dimensional cell region is formed in each of the second seed positions.

DESCRIPTION OF EMBODIMENTS

An image processing device 10, a cell recognition apparatus 100, and a cell recognition method according to an embodiment of the present invention are explained below with reference to the drawings.

Figure 1:
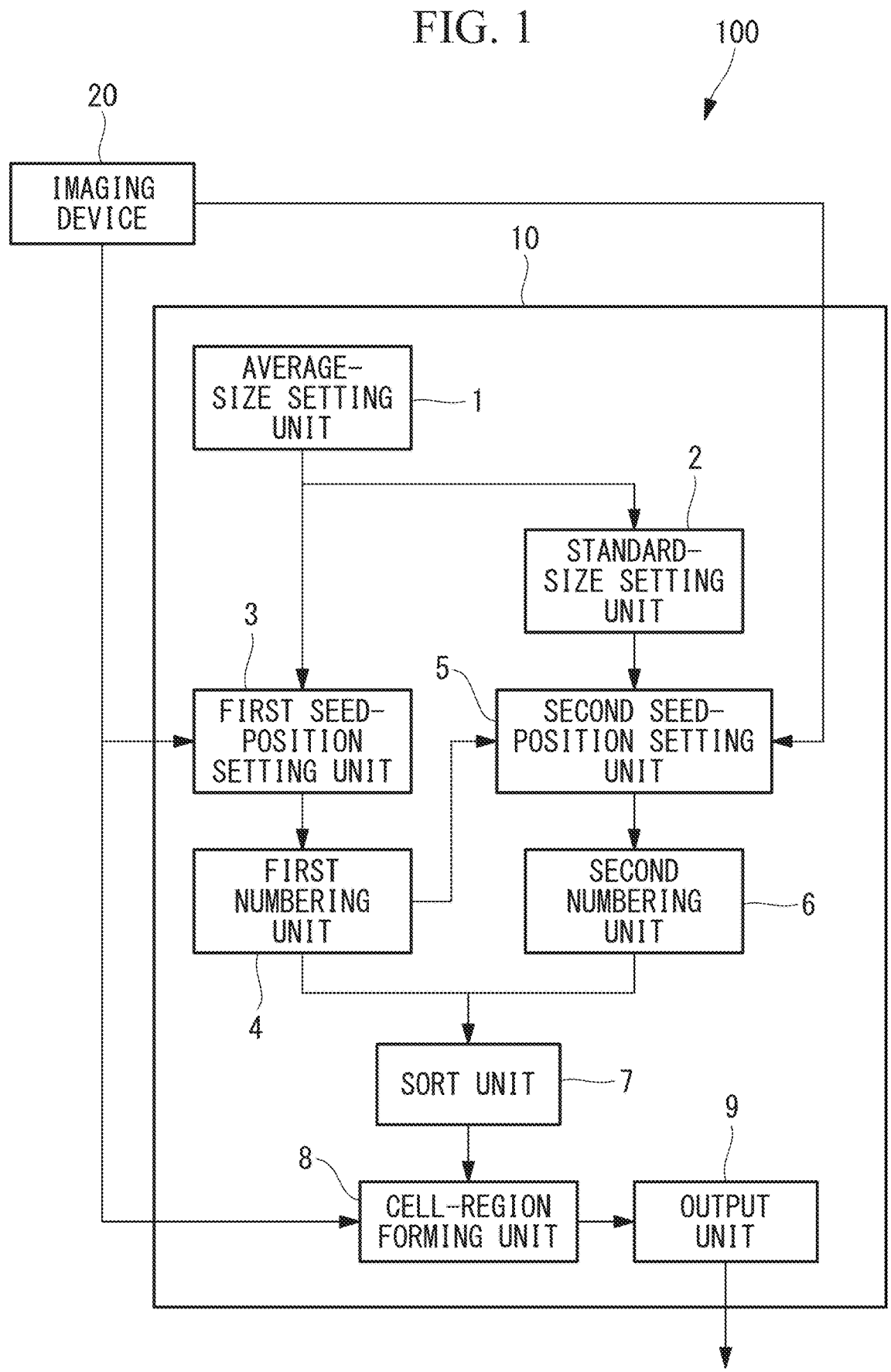
FIG. 1 is a block diagram showing an overall configuration of a cell recognition apparatus according to an embodiment of the present invention.

The cell recognition apparatus 100 according to this embodiment includes, as shown in FIG. 1, an imaging device (an imaging unit) 20 that acquires an image of a cell and the image processing device 10 that processes the image acquired by the imaging device 20.

The imaging device 20 photographs a cell conglomerate and acquires an image. The cell conglomerate is an aggregate of a plurality of cells. Specifically, the imaging device 20 includes an imaging element (not shown in FIG. 1) such as a CCD image sensor and an analog digital (A/D) converter (not shown in FIG. 1). The imaging device 20 converts an optical image of the cell conglomerate generated by an optical microscope into a digital signal through the imaging element and the AD converter and generates a two-dimensional image. The two-dimensional image is, for example, a 16-bit depth image. The optical microscope is, for example, a fluorescence microscope. Therefore, individual cells are represented as regions having higher pixel values than the periphery in the two-dimensional image.

The imaging device 20 acquires a plurality of two-dimensional images in a plurality of Z positions a predetermined interval ΔZ apart from one another in a Z direction and outputs Z stack image data including a set of the plurality of two-dimensional images (slice images) stacked in the Z direction (a stack direction).

Figure 2:
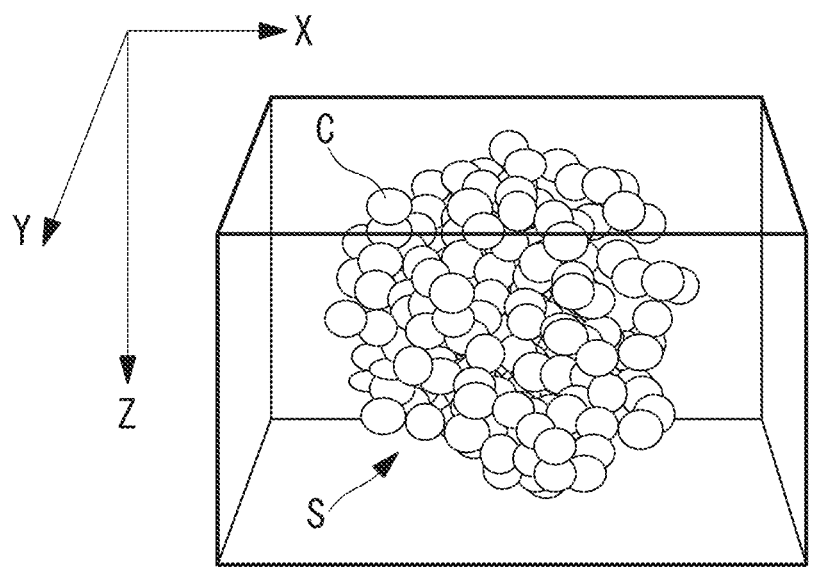
FIG. 2 is a diagram showing an example of a spheroid in which cells are three-dimensionally aggregated in a lump-shape.
Figure 3A:
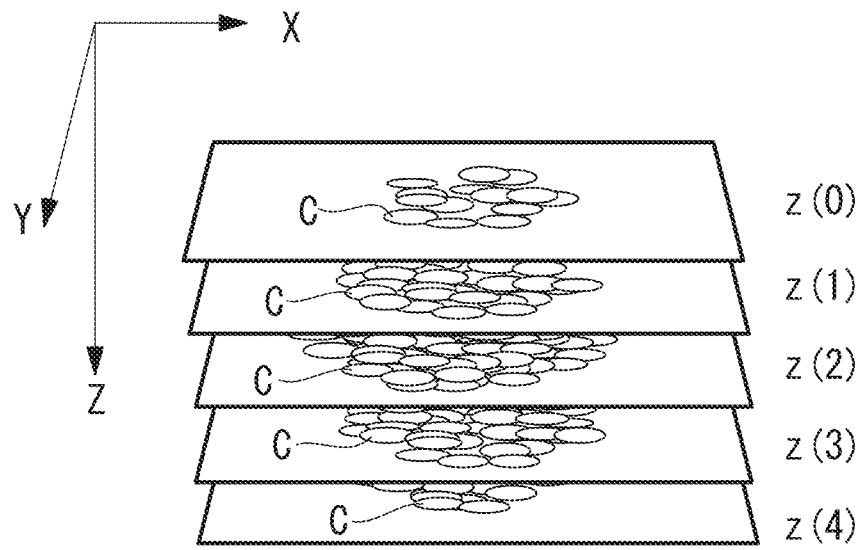
FIG. 3A is a diagram showing an example of a Z stack image formed by a plurality of slice images obtained by photographing the spheroid at a predetermined interval.
Figure 3B:
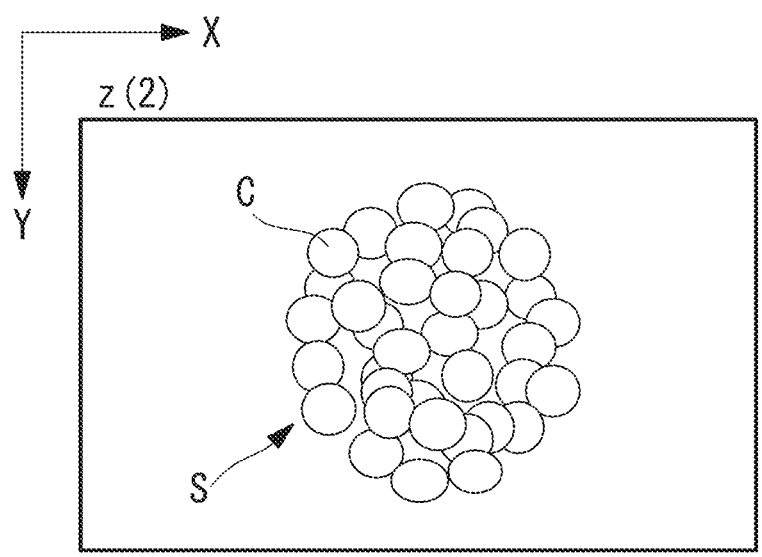
FIG. 3B is a diagram showing a slice image at Z=z(2) in the Z stack image in FIG. 3A.

FIG. 2 shows an example of a spheroid S in which a plurality of cells C are three-dimensionally aggregated. FIG. 3A shows a Z stack image of the spheroid S shown in FIG. 2. FIG. 3B shows one of slice images included in the Z stack image shown in FIG. 3A. The Z direction is a direction extending along optical axes of the optical microscope and the imaging device 20. An X direction and a Y direction are directions orthogonal to the Z direction and orthogonal to each other. The slice image is an image of an XY plane.

As explained below, the imaging device 20 is connected to a first seed-position setting unit 3, a second seed-position setting unit 5, and a cell-region forming unit 8 in the image processing device 10. The Z stack image data output from the imaging device 20 is transmitted to the first seed-position setting unit 3, the second seed-position setting unit 5, and the cell-region forming unit 8.

The image processing device 10 includes an average-size setting unit 1, a standard-size setting unit 2, the first seed-position setting unit 3, a first numbering unit 4, the second seed-position setting unit 5, a second numbering unit 6, a sort unit 7, the cell-region forming unit 8, and an output unit 9.

The average-size setting unit 1 is connected to the standard-size setting unit 2 and the first seed-position setting unit 3. The first seed-position setting unit 3 is connected to the first numbering unit 4. The first numbering unit 4 is connected to the second seed-position setting unit 5 and the sort unit 7. The second seed-position setting unit 5 is connected to the second numbering unit 6. The second numbering unit 6 is connected to the sort unit 7. The sort unit 7 is connected to the cell-region forming unit 8. The cell-region forming unit 8 is connected to the output unit 9.

The processing units 1 to 9 of the image processing device 10 are connected to a not-shown system controller. The operations of the processing units 1 to 9 are controlled by the system controller.

The image processing device 10 may be a computer including a processor such as a CPU (central processing unit), a main storage device such as a RAM, and an auxiliary storage device such as a ROM. A cell recognition program for causing the processor to execute processing in steps S1 to S9 explained below is stored in the auxiliary storage device. The processor executes the processing according to the cell recognition program, whereby functions of the processing units 1 to 9 are realized.

Figure 4A:
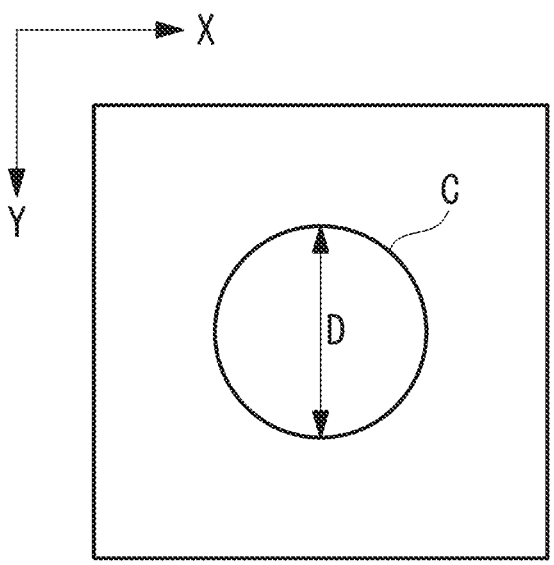
FIG. 4A is a diagram for explaining an average size of a cell.

The average-size setting unit 1 sets an average size D of the cells C in the Z stack image. As shown in FIG. 4A, the average size D is an average diameter on the XY plane of the cell C in the stack image. For example, the image processing device 10 includes a graphical user interface (GUI) operated by a user. The user can input a value of the average size D to the image processing device 10 according to operation of the GUI. The average-size setting unit 1 sets the average size D based on the value input to the image processing device 10 by the user. The average size D is transmitted to the standard-size setting unit 2 and the first seed-position setting unit 3.

Figure 4B:
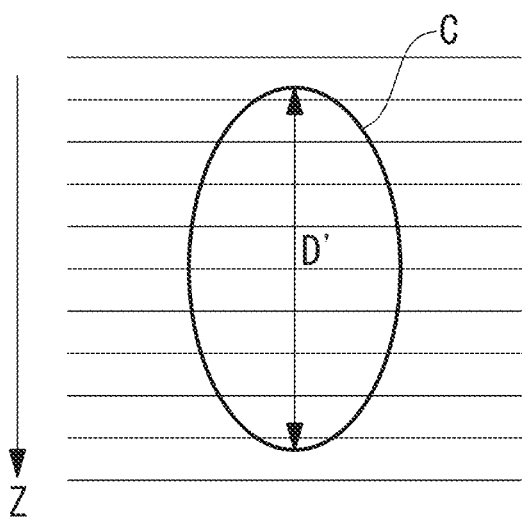
FIG. 4B is a diagram for explaining a standard size of a cell.

The standard-size setting unit 2 receives the average size D of the cells C from the average-size setting unit 1 and sets a standard size D' based on the average size D. The standard size D' is a size in the Z direction of one cell C as shown in FIG. 4B. The standard size D' is calculated by multiplying the average size D by a predetermined coefficient. For example, when optical blur in the Z direction is large and the cell C is apparently an ellipsoid expanding in an upper Z direction, the predetermined coefficient is an expansion ratio of an image in the Z direction. Note that the user may be able to independently set the standard size D' irrespective of the average size D. The standard size D' is transmitted to the second seed-position setting unit 5.

The first seed-position setting unit 3 detects pixels, pixel values of which indicate three-dimensional peaks, out of the Z stack image and sets positions of the detected pixels as parent seed positions (first seed positions) P1. Pixel values in the individual cells C in the Z stack image are the highest in the center portions of the cells C and decrease away from the center portions. Therefore, the parent seed positions P1 are set in the center portions of the individual cells C in the Z stack image.

Figure 5:
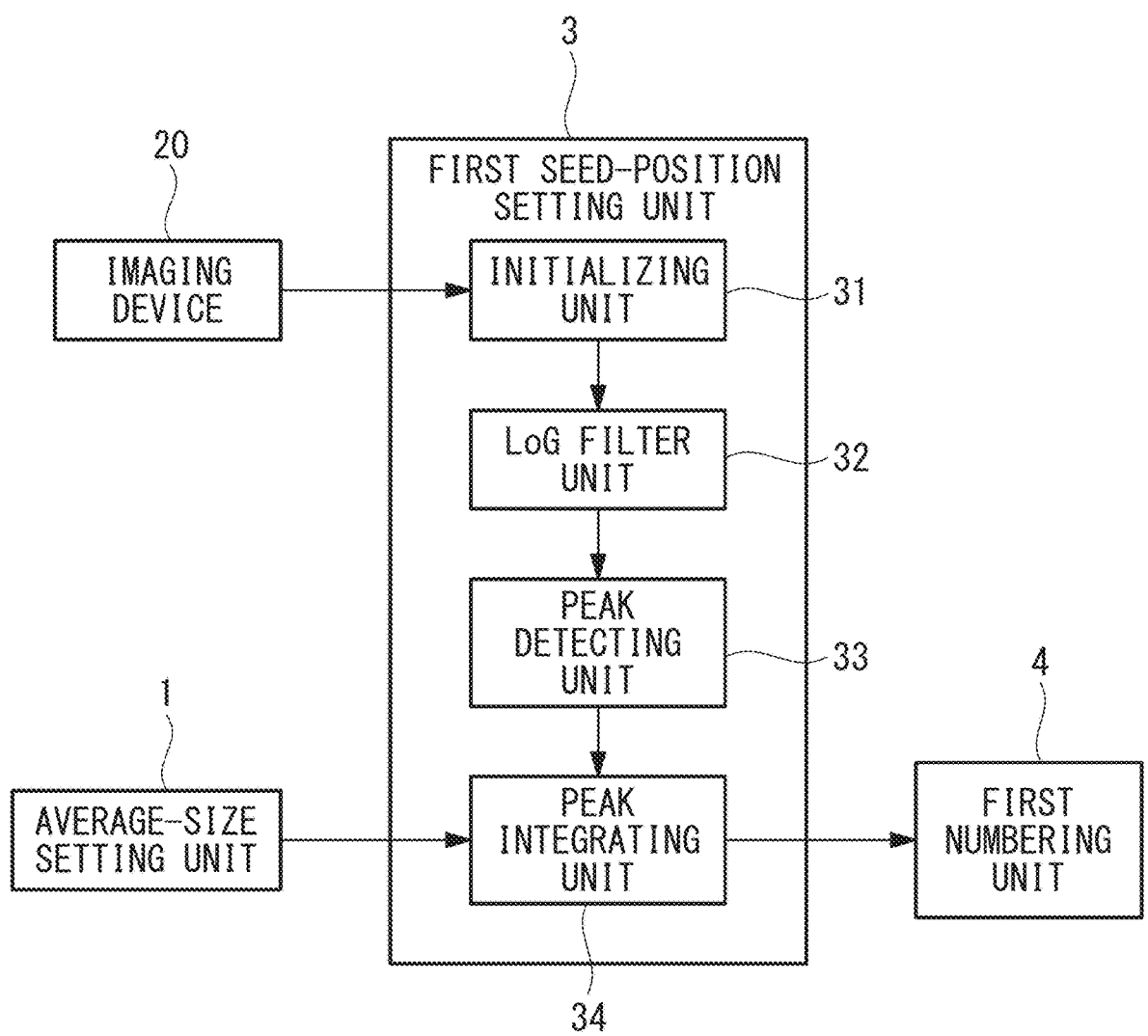
FIG. 5 is a block diagram showing a specific configuration of a first seed-position setting unit in the cell recognition apparatus shown in FIG. 1.

Specifically, the first seed-position setting unit 3 includes, as shown in FIG. 5, an initializing unit 31, a LoG filter unit (a feature-value calculating unit) 32, a peak detecting unit 33, and a peak integrating unit 34.

The imaging device 20 is connected to the initializing unit 31. The initializing unit 31 is connected to the LoG filter unit 32. The LoG filter unit 32 is connected to the peak detecting unit 33. The average-size setting unit 1 and the peak detecting unit 33 are connected to the peak integrating unit 34. The peak integrating unit 34 is connected to the first numbering unit 4.

The initializing unit 31 reads the Z stack image transmitted from the imaging device 20 and initializes (normalizes) a pixel value of each pixel to a 12-bit depth width, that is, adjusts the pixel value to a gradation width 0 to 4095 range. Specifically, the initializing unit 31 detects a maximum value max of pixel values in the Z stack image and multiplies each pixel value by a gain (=4095/max). Initialized Z stack image data is transmitted to the LoG filter unit 32.

The LoG filter unit 32 receives the initialized Z stack image from the initializing unit 31 and applies a LoG (Laplacian of Gaussian) filter to the initialized Z stack image. The LoG filter has an effect obtained by combining a Gaussian filter (a smoothing filter) and a Laplacian filter (a secondary differential (edge detection) filter).

The following expression is an example of the two-dimensional LoG filter.

$$\text{LoG}(x,y) = (x^2+y^2-2\sigma^2)/(2\pi\sigma^6) \times \exp\{-(x^2+y^2)/(2\sigma^2)\},$$

where x and y are positions of pixels. LoG(x, y) is a filter output value (a feature value; hereinafter referred to as LoG output value) and σ is a parameter for adjusting a filter effect.

In the stack image, the cell C is represented as a bright spot having a pixel value higher than a pixel value of the periphery. The LoG output value represents likelihood of a pixel value being an extreme value. The LoG output value is larger in a peak position of the pixel value than in a peripheral pixel. Therefore, the LoG filter can be used when the peak position of the pixel value is detected as a position of the cell C.

The LoG filter unit 32 applies the two-dimensional LoG filter to each slice image of the initialized Z stack image, calculates a LoG output value of each pixel, and generates a LoG output value image having the LoG output value as a pixel value. The LoG output value image is transmitted to the peak detecting unit 33.

The LoG filter unit 32 may apply a three-dimensional LoG filter to a three-dimensional Z stack image instead of applying the two-dimensional LoG filter to the two-dimensional slice image.

The peak detecting unit 33 receives the LoG output value image from the LoG filter unit 32 and detects, from the LoG output value image, a peak pixel, the LoG output value of which locally indicates a maximum value. Specifically, the peak detecting unit 33 three-dimensionally scans a slice image in each Z position of the LoG output value image and detects a peak pixel, a LoG output value of which is higher than LoG output values of peripheral pixels adjacent to the peak pixel in the X, Y, and Z directions. A position of the peak pixel is a candidate position of the parent seed position P1. Subsequently, the peak detecting unit 33 creates parent seed information including an XYZ coordinate of a position in a three-dimensional space and the LoG output value of the peak pixel. The parent seed information is transmitted to the peak integrating unit 34.

The peak integrating unit 34 receives the parent seed information from the peak detecting unit 33 and receives the average size D of the cells C from the average-size setting unit 1. Subsequently, when two peak pixels extremely close to each other are present in the parent seed information, the peak integrating unit 34 integrates the two peak pixels into one.

Specifically, the peak integrating unit 34 selects coordinates of the two peak pixels from the parent seed information and calculates a spatial distance between the two coordinates. Subsequently, when the spatial distance is equal to or smaller than a threshold, the peak integrating unit 34 determines that the two peak pixels are sufficiently close compared with the average size D of the cells C and integrates the two peak pixels. The threshold is set based on the average size D.

In the integration of the two peak pixels, the peak integrating unit 34 compares LoG output values of the two peak pixels and determines that the peak pixel having a larger LoG output value is more likely to be the parent seed position P1 (i.e., closer to the center position of the cell C). The peak integrating unit 34 leaves, in the parent seed information, the coordinate and the LoG output value of the peak pixel having the larger LoG output value and deletes the coordinate and the LoG output value of the other peak pixel from the parent seed information. There is possibility that a position other than the center portion of the cell C is erroneously detected as a peak pixel because of noise or the like. A coordinate of the erroneously detected peak pixel is deleted from the parent seed information by the integration of the two peak pixels close to each other.

The peak integrating unit 34 comprehensively performs, for all the peak pixels included in the parent seed information, retrieval and integration of peak pixels close to each other and repeats the retrieval and the integration until there are no more peak values to be integrated. A position of a peak value remaining in the parent seed information after the integration of the peak pixels is finally set as the parent seed position P1. The integrated parent seed information is transmitted to the first numbering unit 4.

The first numbering unit 4 receives the parent seed information from the peak integrating unit 34 and gives a unique identification number to each of the parent seed positions P1 included in the parent seed information. The identification number is a region number for identifying a three-dimensional cell region formed by the cell-region forming unit 8 explained below. The first numbering unit 4 adds identification numbers to the parent seed positions P1, for example, in descending order of pixel values. The parent seed information, in which the identification numbers are added to the parent seed positions P1, is transmitted to the second seed-position setting unit 5 and the sort unit 7.

Figure 6:
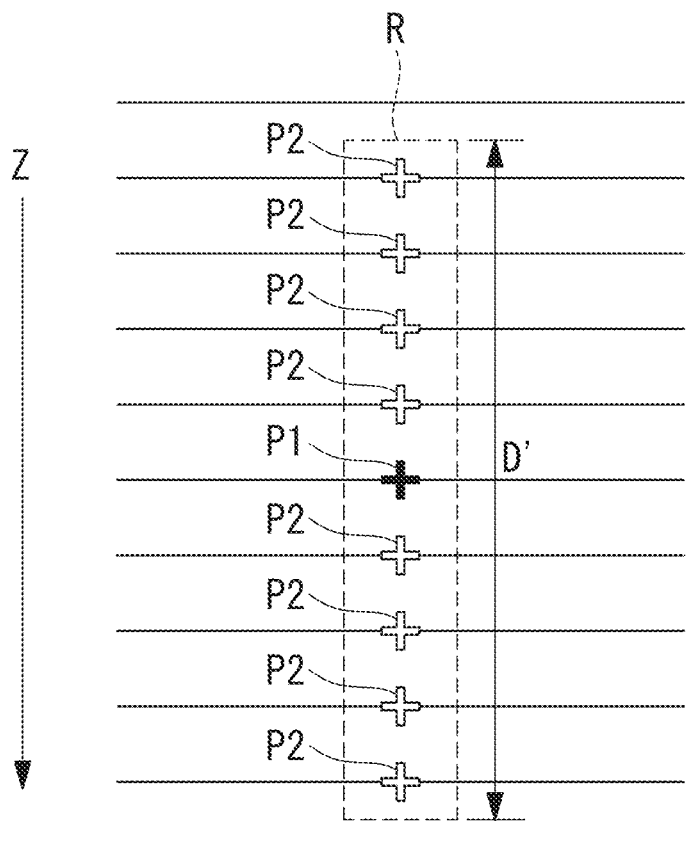
FIG. 6 is a diagram for explaining a positional relation between a parent seed and a child seed.

The second seed-position setting unit 5 sets, referring to the parent seed positions P1 included in the parent seed information, child seed positions (second seed positions) P2 within a range R of the standard size D' centering on each parent seed position P1. As shown in FIG. 6, the child seed positions P2 are positions shifted in the Z direction with respect to the parent seed position P1 within the same range R, which is a reference source of the child seed positions P2. That is, only Z coordinates of the child seed positions P2 and the parent seed position P1 within the same range R are different. The child seed positions P2 are set on both sides in the Z direction of the parent seed position P1 while being spaced apart by a predetermined number of pixels equivalent to the interval ΔZ between the slice images. Therefore, each child seed position P2 is a position on the slice image. In the example shown in FIG. 6, four child seed positions P2 are set on each of both sides of the parent seed position P1. The second seed-position setting unit 5 creates child seed information including the child seed positions P2.

Figure 7:
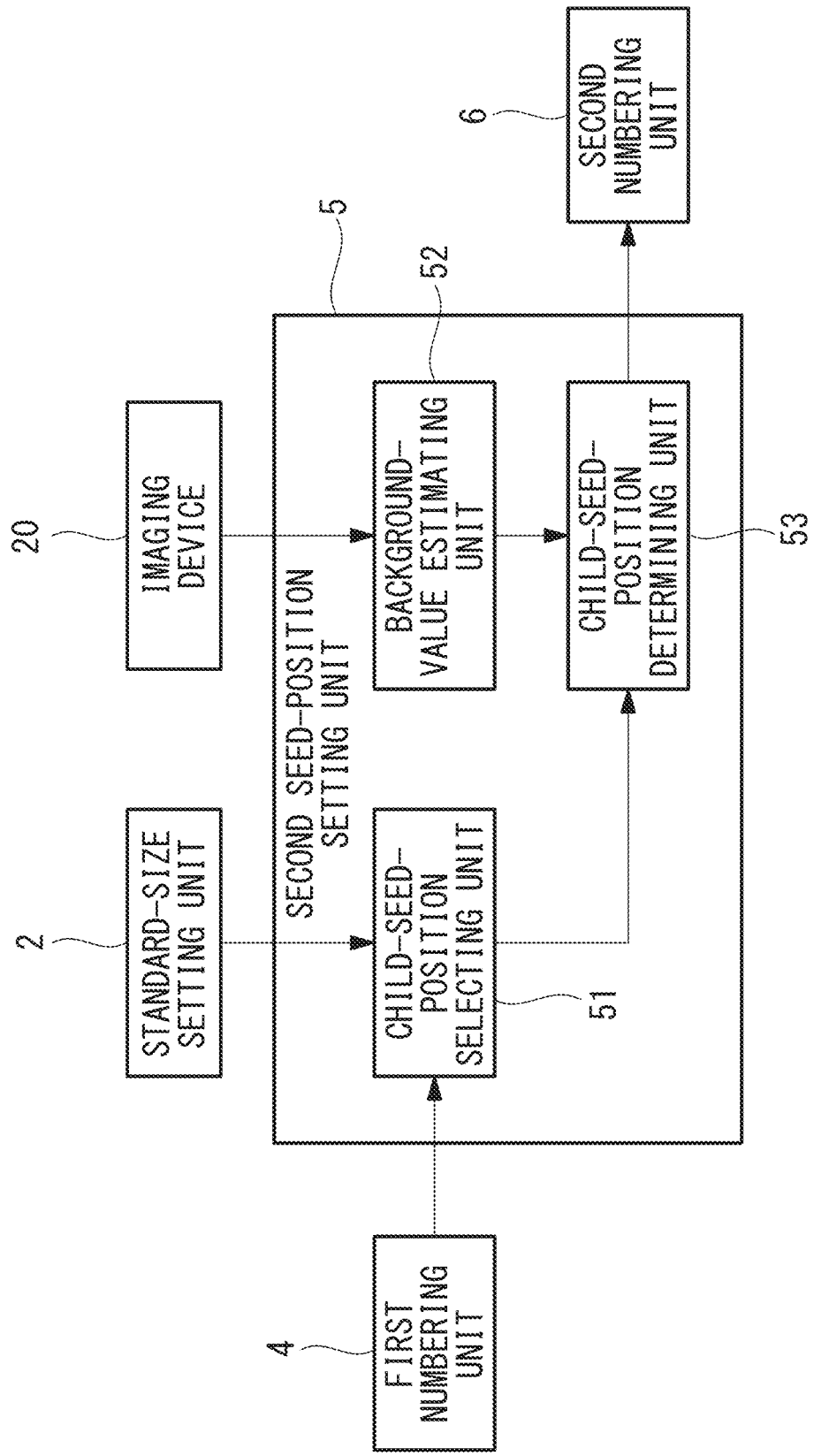
FIG. 7 is a block diagram showing a specific configuration of a second seed-position setting unit in the cell recognition apparatus shown in FIG. 1.

Specifically, the second seed-position setting unit 5 includes, as shown in FIG. 7, a child-seed-position selecting unit 51, a background-value estimating unit 52, and a child-seed-position determining unit 53.

The first numbering unit 4 and the standard-size setting unit 2 are connected to the child-seed-position selecting unit 51. The imaging device 20 is connected to the background-value estimating unit 52. The child-seed-position selecting unit 51 and the background-value estimating unit 52 are connected to the child-seed-position determining unit 53. The child-seed-position determining unit 53 is connected to the second numbering unit 6.

The child-seed-position selecting unit 51 receives parent seed information from the first seed-position setting unit 3. Subsequently, the child-seed-position selecting unit 51 selects the child seed positions P2 from the range R centering on each parent seed position P1 in the stack image. The child seed positions P2 to be selected are positions each shifted by a predetermined number of pixels (one stack) in the Z direction from the parent seed position P1 and are candidate positions of final child seed positions P2. The second seed-position setting unit 5 creates child seed information. The child seed information includes XYZ coordinates of the selected child seed positions P2, distances from the parent seed position P1, which is a reference source of each child seed position P2, (i.e., shift amounts in the Z direction from the parent seed position P1), and pixel values of the Z stack image in the child seed positions P2. The child seed information is transmitted to the child-seed-position determining unit 53.

The background-value estimating unit 52 receives the stack image from the imaging device 20 and estimates a background pixel value of the Z stack image. The background pixel value is an average pixel value of a background region not including the cell C. A publicly-known method is used for the estimation of the background pixel value. For example, a pixel value of the Z stack image is binarized, a dark region is specified as the background region, and an average pixel value of a region corresponding to the background region in the Z stack image is calculated as a background pixel value. A threshold used for the binarization is calculated by, for example, the Otsu method. When a ratio of a volume of the cell C in the Z stack image is extremely small, an average pixel value of the Z stack image may be used as the background pixel value. The background pixel value is transmitted to the child-seed-position determining unit 53.

The child-seed-position determining unit 53 receives the child seed information from the child-seed-position selecting unit 51 and receives the background pixel value from the background-value estimating unit 52. Subsequently, the child-seed-position determining unit 53 compares pixel values of the child seed positions P2 in the child seed information with the background pixel value (a predetermined value). When the child seed positions P2 are positions in the cell, the pixel values of the child seed positions P2 are larger than the background pixel value. On the other hand, when the child seed positions P2 are positions in the background region, the pixel values of the child seed positions P2 are equal to or smaller than the background pixel value. The child-seed-position determining unit 53 leaves coordinates, distances, and pixel values of the child seed positions P2, the pixel values of which are larger than the background pixel values, in the child seed information and deletes coordinates, distances, and pixel values of the child seed positions P2, the pixel values of which are equal to or smaller than the background pixel value, from the child seed information. The child-seed-position determining unit 53 performs comparison with the background pixel value, for example, in order from the child seed position P2 at the shortest distance from the parent seed position P1.

As a result of the processing explained above, data concerning the child seed positions P2 in the background region among the child seed positions P2 selected from the range R is deleted from the child seed information. After the determination processing is performed about all the child seed positions P2 in the child seed information, coordinates, distances, and pixel values of the finally remaining child seed positions P2 are transmitted to the second numbering unit 6 as the child seed information.

The second numbering unit 6 receives the child seed information from the child-seed-position determining unit 53. Subsequently, the second numbering unit 6 sets, in each child seed position P2 in the child seed information, the same identification number as the identification number of the parent seed position P1 in the same range R, which is the reference source. Consequently, the same identification numbers are set in the parent seed position P1 and the child seed positions P2 within one range R corresponding to one cell C. The child seed information in which the identification numbers are given to the child seed positions P2 is transmitted to the sort unit 7.

The sort unit 7 receives the parent seed information from the first numbering unit 4 and receives the child seed information from the second numbering unit 6. Subsequently, the sort unit 7 integrates the parent seed information and the child seed information into one and rearranges the seed positions P1 and P2 to thereby determine formation order of two-dimensional cell regions by the cell-region forming unit 8.

Specifically, the sort unit 7 sets a distance in the Z direction of each parent seed position P1 from the parent seed position P1 of the reference source (i.e., the parent seed position P1 itself) to zero and integrates the parent seed positions P1 and the child seed positions P2. Subsequently, the sort unit 7 rearranges the parent seed positions P1 and the child seed positions P2 in ascending order of a distance from the parent seed position P1 without distinguishing the parent seed positions P1 and the child seed positions P2 and creates sorted seed information. Since the distance of each parent seed position P1 is zero, in the sorted seed information, the parent seed positions P1 are located in higher order and the child seed positions P2 are located lower in order than all the parent seed positions P1. The sorted seed information is transmitted to the cell-region forming unit 8.

Figure 8:
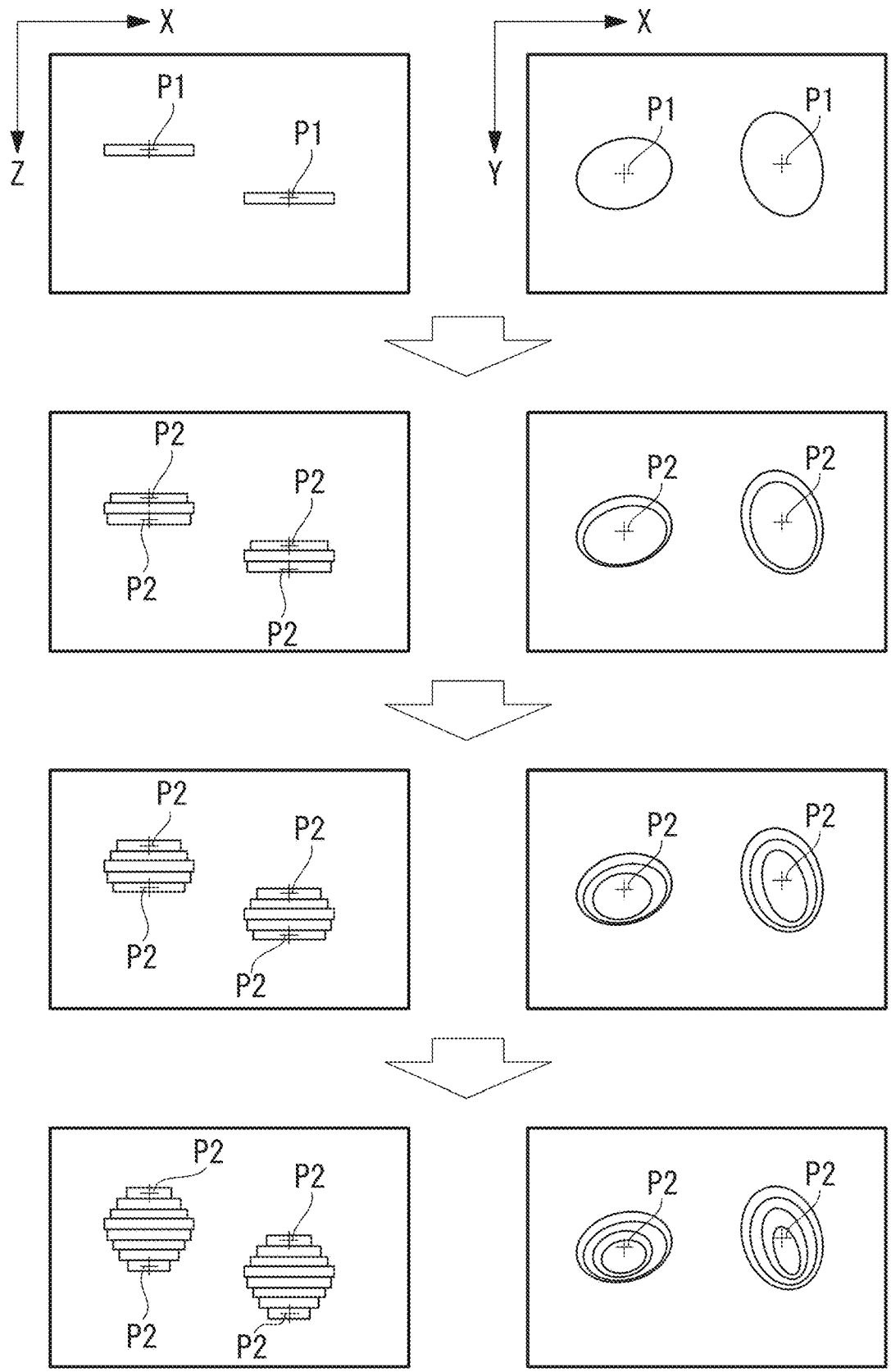
FIG. 8 is a diagram showing forming order of two-dimensional cell regions and a forming process for a three-dimensional cell region.

The cell-region forming unit 8 receives the sorted seed information from the sort unit 7 and selects seed positions in the sorted seed information one by one in order from the top. Subsequently, the cell-region forming unit 8 forms, based on a pixel value distribution of peripheral pixels of a selected seed position, a two-dimensional cell region in the selected seed position. The two-dimensional cell region is formed on a slice image including the selected seed position. Since the cell-region forming unit 8 selects the seed positions in the sorted seed information in order from the top, two-dimensional cell regions are formed in all the parent seed positions P1 and thereafter two-dimensional cell regions are formed in the child seed positions P2. Therefore, as shown in FIG. 8, two-dimensional cell regions are formed in order from the center portion of the cell C toward both sides in the Z direction. Finally, a three-dimensional cell region is formed from a plurality of two-dimensional cell regions stacked in the Z direction.

Figure 9:
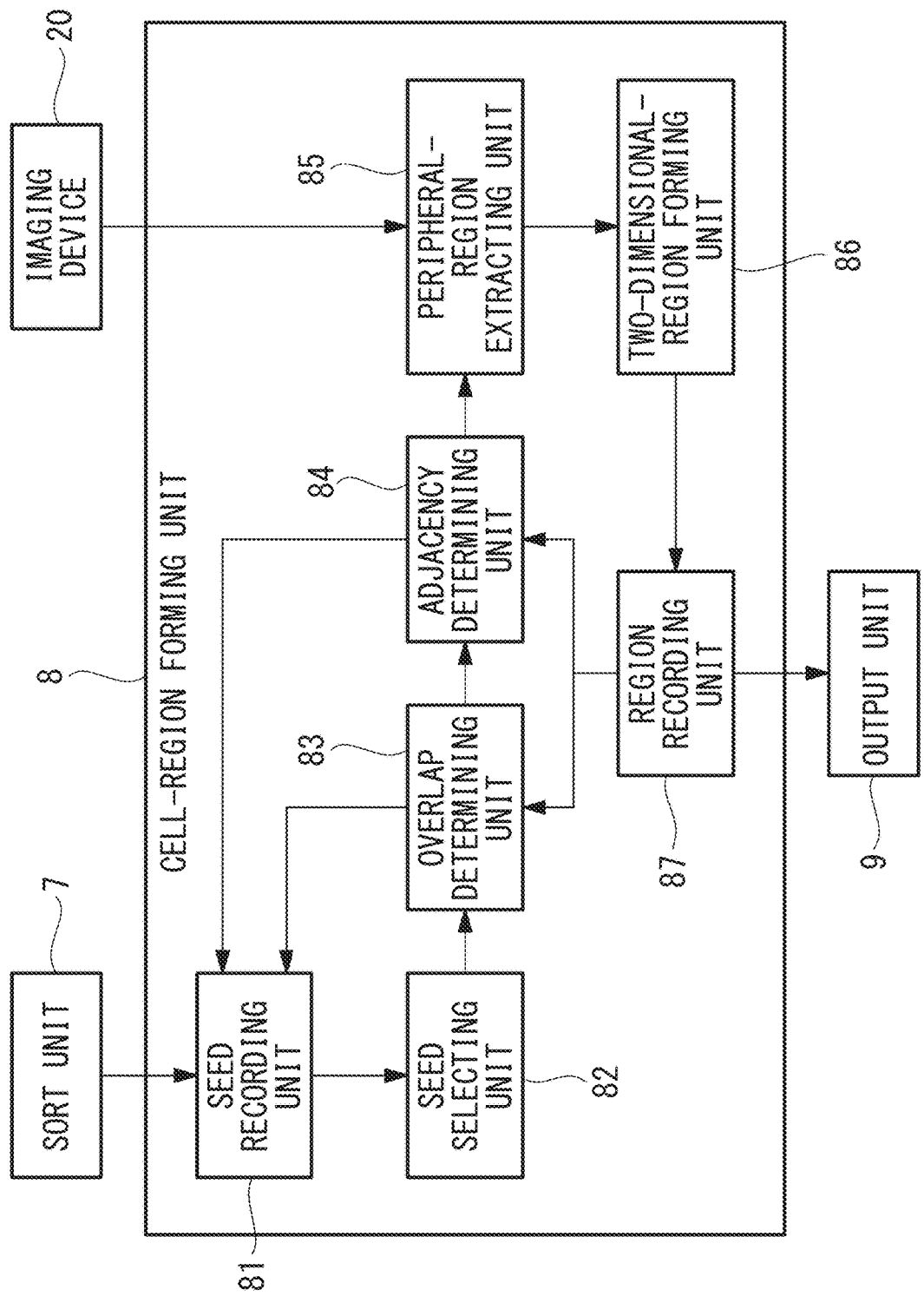
FIG. 9 is a block diagram showing a specific configuration of a cell-region forming unit in the cell recognition apparatus shown in FIG. 1.

Specifically, the cell-region forming unit 8 includes, as shown in FIG. 9, a seed recording unit 81, a seed selecting unit 82, an overlap determining unit 83, an adjacency determining unit 84, a peripheral-region extracting unit 85, a two-dimensional-region forming unit 86, and a region recording unit 87.

The sort unit 7, the overlap determining unit 83, and the adjacency determining unit 84 are connected to the seed recording unit 81. The seed recording unit 81 is connected to the seed selecting unit 82. The seed selecting unit 82 and the region recording unit 87 are connected to the overlap determining unit 83. The overlap determining unit 83 and the region recording unit 87 are connected to the adjacency determining unit 84. The adjacency determining unit 84 and the imaging device 20 are connected to the peripheral-region extracting unit 85. The peripheral-region extracting unit 85 is connected to the two-dimensional-region forming unit 86. The two-dimensional-region forming unit 86 is connected to the region recording unit 87. The region recording unit 87 is connected to the output unit 9.

The seed recording unit 81 is a buffer memory that temporarily records the sorted seed information received from the sort unit 7. The sorted seed information recorded in the seed recording unit 81 is updated according to determination results by the overlap determining unit 83 and the adjacency determining unit 84.

The seed selecting unit 82 selects seed positions in the sorted seed information recorded in the seed recording unit 81 one by one in order from the top and transmits the selected seed position to the overlap determining unit 83.

The overlap determining unit 83 receives the seed position from the seed selecting unit 82. Subsequently, the overlap determining unit 83 determines whether a two-dimensional cell region is already formed by the two-dimensional-region forming unit 86 in the received seed position. The two-dimensional cell region formed by the two-dimensional-region forming unit 86 is recorded in the region recording unit 87 as explained below. The overlap determining unit 83 performs the determination based on two-dimensional cell regions recorded in the region recording unit 87 up to the present point in time. When a two-dimensional cell region is already formed in the seed position, the overlap determining unit 83 does not transmits the seed position to the adjacency determining unit 84 and deletes data concerning the seed position from the sorted seed information in the seed recording unit 81. Consequently, processing related to formation of a two-dimensional cell region in the seed position is cancelled. Another two-dimensional cell region is prevented from being redundantly formed in a region where a two-dimensional cell region is already present. On the other hand, when a two-dimensional cell region is not formed in the seed position yet, the overlap determining unit 83 transmits the seed position to the adjacency determining unit 84.

The adjacency determining unit 84 receives the seed position from the overlap determining unit 83. When a distance of the seed position from the parent seed position P1 is zero (i.e., when the seed position is the parent seed position P1), the adjacency determining unit 84 does not perform determination processing explained below and transmits the seed position to the peripheral-region extracting unit 85. When the distance of the seed position from the parent seed position P1 is not zero (i.e., the seed position is the child seed position P2), the adjacency determining unit 84 determines whether a two-dimensional cell region is already formed by the two-dimensional-region forming unit 86 in a position adjacent to the seed position in the Z direction. When a two-dimensional cell region is already formed in the adjacent position, the adjacency determining unit 84 further determines whether an identification number (a region number) of the two-dimensional cell region is the same as an identification number of the seed position.

When a two-dimensional cell region is not formed in the adjacent position or the identification number of the two-dimensional cell region in the adjacent position is different, the adjacency determining unit 84 does not transmit the seed position to the peripheral-region extracting unit 85 and deletes the seed position and information related to the seed position from the sorted seed information in the seed recording unit 81. Consequently, the processing related to formation of a two-dimensional cell region in the seed position is cancelled. A discontinuous three-dimensional cell region is prevented from being formed in the Z direction.

On the other hand, when a two-dimensional cell region is already formed in the position adjacent to the seed position in the Z direction and an identification number of the two-dimensional cell region is the same as the identification number of the seed position, the adjacency determining unit 84 transmits the seed position to the peripheral-region extracting unit 85.

Figure 10A:
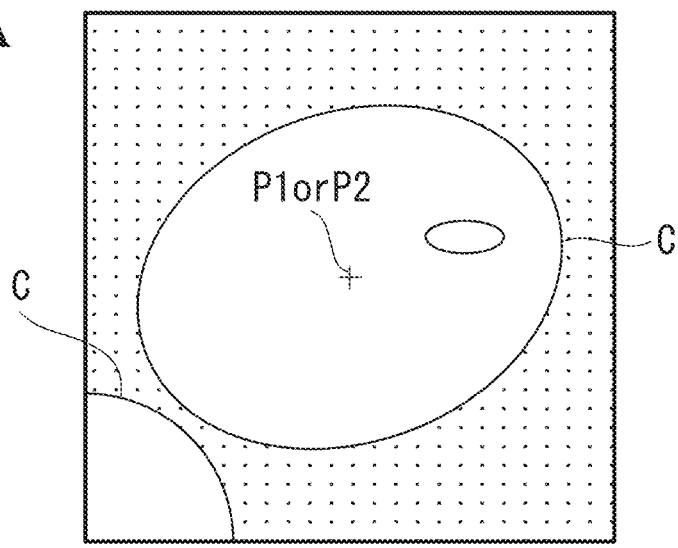
FIG. 10A is a diagram, for explaining a forming method for a two-dimensional cell region by threshold processing of a pixel value, showing a trimming image.

The peripheral-region extracting unit 85 receives the Z stack image from the imaging device 20 and receives the seed position from the adjacency determining unit 84. Subsequently, the peripheral-region extracting unit 85 selects, from the Z stack image, a slice image in which the seed position is located. Subsequently, the peripheral-region extracting unit 85 segments, from the slice image, a region in a predetermined range centering on the seed position and including the cells C and generates a trimming image as shown in FIG. 10A. A size of the region to be segmented is set based on the average size D of the cells C and is, for example, a size obtained by multiplying the average size D by a predetermined coefficient. The trimming image is transmitted to the two-dimensional-region forming unit 86.

Figure 10B:
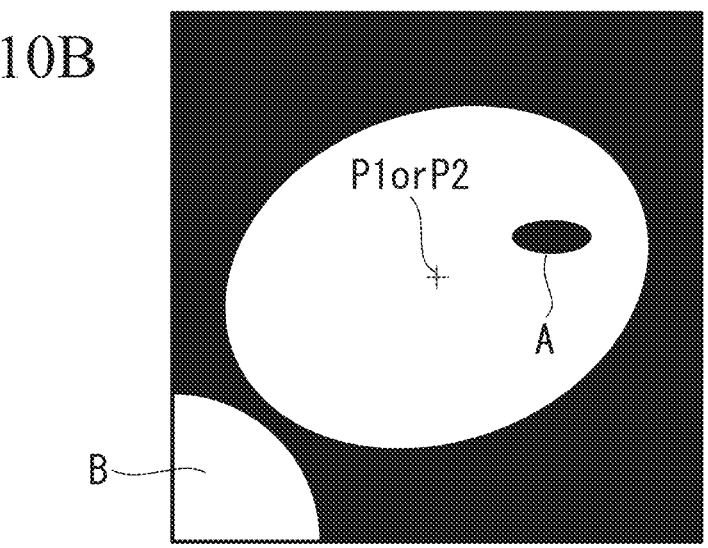
FIG. 10B is a diagram, for explaining a forming method for a two-dimensional cell region by threshold processing of a pixel value, showing a binarized image after the threshold processing.

The two-dimensional-region forming unit 86 receives the trimming image from the peripheral-region extracting unit 85. As shown in FIG. 10B, the two-dimensional-region forming unit 86 binarizes a pixel value by applying threshold processing to the trimming image. That is, the two-dimensional-region forming unit 86 converts a pixel value equal to or larger than a threshold into "1" and converts a pixel value smaller than the threshold into "0". The two-dimensional-region forming unit 86 may apply smoothing processing by a smoothing filter or the like to the trimming image and apply the threshold processing to the smoothed trimming image. As shown in FIG. 10B, in the binarized trimming image, a region where the pixel value is "0" is represented by black and a region where the pixel value is "1" is represented by white. A cell relatively has a large pixel value and is represented as a white region. A background is represented as a black region. A two-dimensional cell region is formed from the white region in the binarized trimming image. The binarized trimming image including the two-dimensional cell region is transmitted to the region recording unit 87 together with the identification number of the seed position and recorded in the region recording unit 87 with the identification number set as a region number.

The two-dimensional-region forming unit 86 may use a preset fixed value as the threshold.

Preferably, the two-dimensional-region forming unit 86 uses, for the threshold processing, an adaptive threshold calculated based on the pixel value of the trimming image. In this case, the two-dimensional-region forming unit 86 creates a histogram of the pixel value of the trimming image. Subsequently, the two-dimensional-region forming unit 86 calculates, based on the histogram, an adaptive threshold according to, for example, the Otsu method.

Figure 10C:
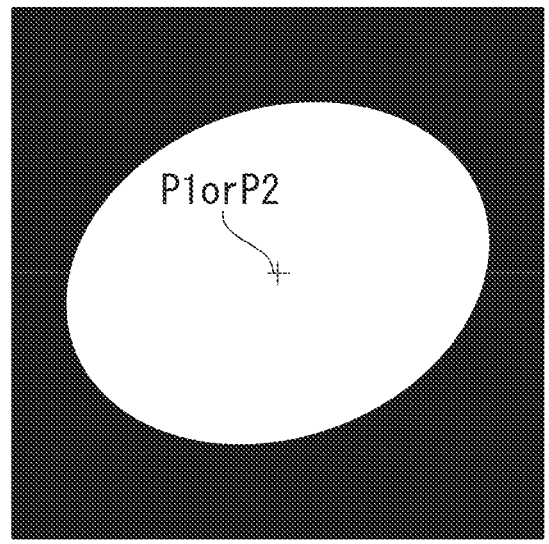
FIG. 10C is a diagram, for explaining a forming method for a two-dimensional cell region by threshold processing of a pixel value, showing a binarized image after post-processing.

The two-dimensional-region forming unit 86 may perform post-processing on the binarized trimming image and cause the region recording unit 87 to record an image after the post-processing. FIG. 10C shows the image after the post-processing of the binarized trimming image shown in FIG. 10B. For example, when a black small region A is present in the white region including the seed position as shown in FIG. 10B, the two-dimensional-region forming unit 86 removes the black small region A by converting a pixel value of the black small region A into a pixel value corresponding to white. When a white region B, which is a portion of a cell in the vicinity, is present in a position far from the seed position, the two-dimensional-region forming unit 86 removes, from the binarized trimming image, the white region B not including the seed position.

Figure 11A:
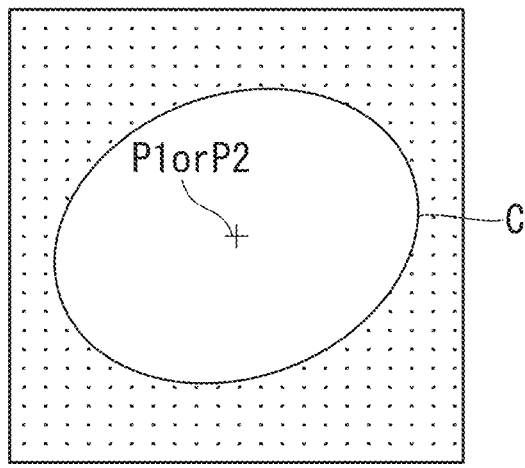
FIG. 11A is a diagram, for explaining a forming method for a two-dimensional cell region by threshold processing of a pixel value gradient, showing a trimming image.
Figure 11B:
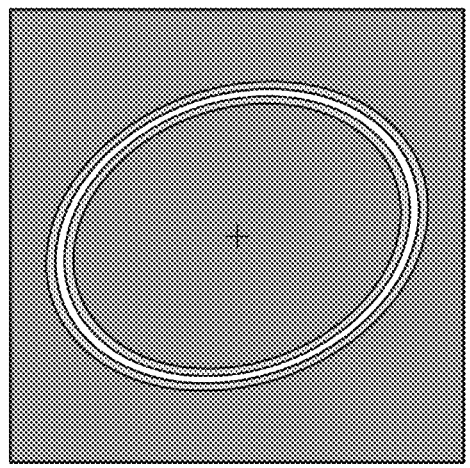
FIG. 11B is a diagram, for explaining a forming method for a two-dimensional cell region by threshold processing of a pixel value gradient, showing a pixel value gradient image.
Figure 11C:
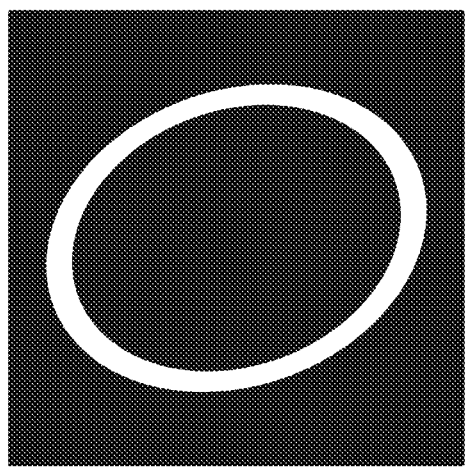
FIG. 11C is a diagram, for explaining a forming method for a two-dimensional cell region by threshold processing of a pixel value gradient, showing a binarized image after the threshold processing.
Figure 11D:
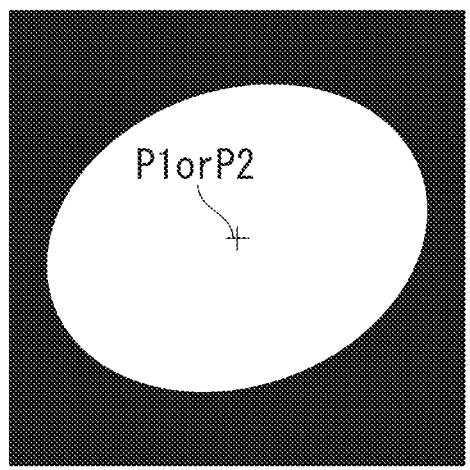
FIG. 11D is a diagram, for explaining a forming method for a two-dimensional cell region by threshold processing of a pixel value gradient, showing a binarized image after post-processing.

A gradient of the pixel value increases in a boundary of the cell C in the trimming image. Therefore, the two-dimensional-region forming unit 86 may perform threshold processing (binarization processing) of the pixel value gradient instead of the threshold processing (the binarization processing) of the pixel value. That is, the two-dimensional-region forming unit 86 calculates a gradient of a pixel value in a position of each pixel in the trimming image (see FIG. 11A) and creates a gradient image in which the gradient of the pixel value is a threshold (see FIG. 11B). Subsequently, the two-dimensional-region forming unit 86 detects a pixel, a gradient of which is equal to or larger than the threshold, as a boundary of the cells C (see FIG. 11C) and sets, as a two-dimensional cell region, a region including the seed position and defined by the boundary (see FIG. 11D).

In this case as well, the two-dimensional-region forming unit 86 may use a preset fixed value as the threshold. However, preferably, the two-dimensional-region forming unit 86 uses an adaptive threshold calculated based on the pixel value of the gradient image. That is, the two-dimensional-region forming unit 86 creates a histogram of the pixel value of the gradient image and calculates, based on the histogram, an adaptive threshold according to, for example, the Otsu method.

The region recording unit 87 is a buffer memory having the same data size as the Z stack image. The region recording unit 87 records the two-dimensional cell region to which the identification number of the seed position is added as the region number. A halfway result of formation of a three-dimensional cell region is recorded in the region recording unit 87. All seed positions in the sorted seed information is selected by the seed selecting unit 82. When processing for a seed position selected last ends, data of a three-dimensional cell region is formed in the region recording unit 87. The three-dimensional cell region is transmitted to the output unit 9 and output to a predetermined display device, recording device, or the like from the output unit 9.

Subsequently, a cell recognition method by the cell recognition apparatus 100 is explained with reference to flowcharts of FIG. 12 to FIG. 15.

Figure 12:
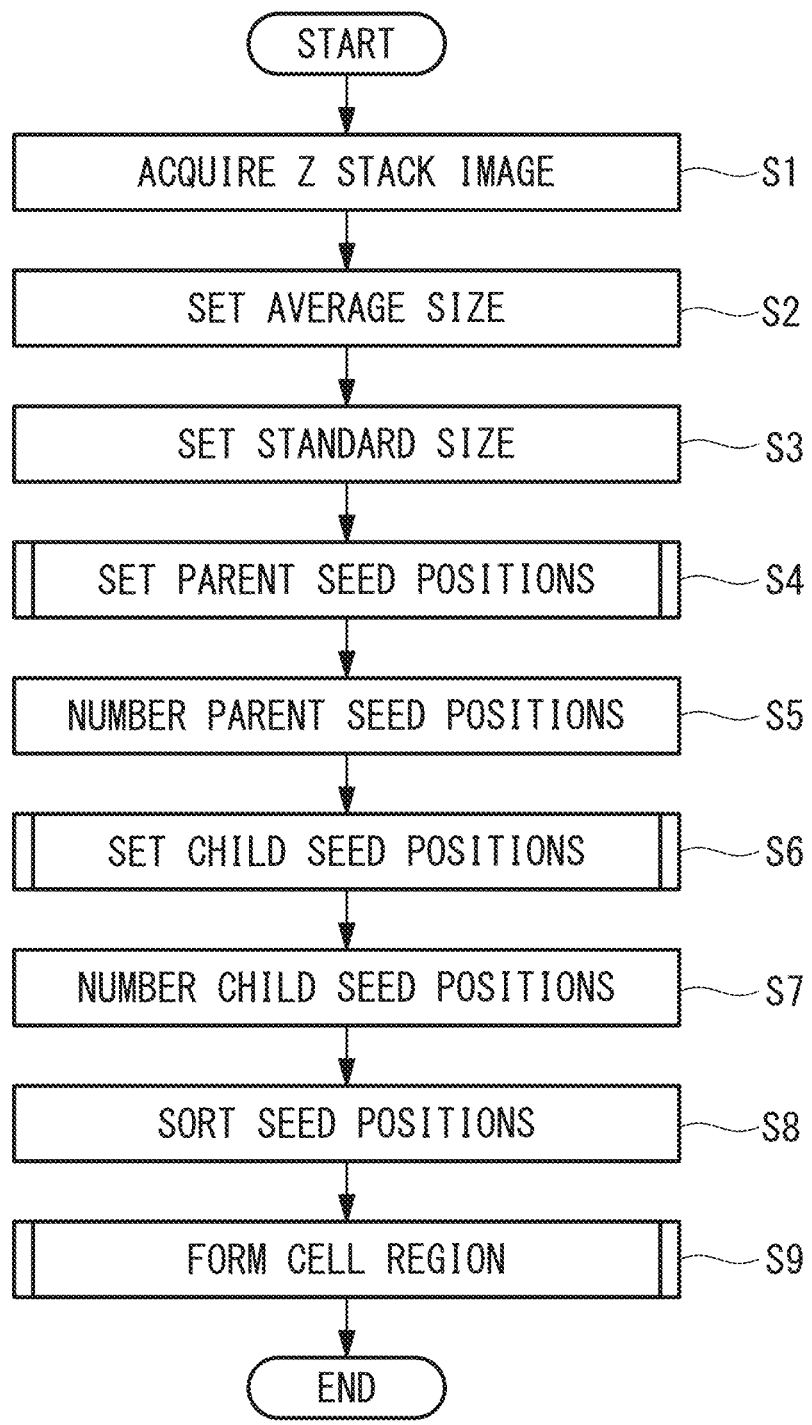
FIG. 12 is a flowchart showing a cell recognition method according to the embodiment of the present invention.

The cell recognition method includes, as shown in FIG. 12, step S1 for acquiring a Z stack image, step S2 for setting the average size D, step S3 for setting the standard size D' of the cell C, step S4 for setting a plurality of parent seed positions P1 in the Z stack image and creating parent seed information, step S5 for giving a unique identification number to each parent seed position P1, step S6 for setting child seed positions P2 in the range R of the standard size D' centering on each parent seed position P1 and creating child seed information, step S7 for giving an identification number to each child seed position P2, step S8 for integrating the parent seed information and the child seed information and rearranging the order of the parent seed positions P1 and the child seed positions P2, and step S9 for forming a two-dimensional cell region in each seed position.

First, in step S1, a Z stack image acquired by the imaging device 20 is input to the image processing device 10.

Subsequently, in step S2, the average size D of the cells C in the Z stack image is set by the average-size setting unit 1.

Subsequently, in step S3, the standard size D' is set based on the average size D by the standard-size setting unit 2.

Subsequently, in step S4, the parent seed position P1 is set in the center portion of each cell C in the Z stack image by the first seed-position setting unit 3 and parent seed information is created.

Figure 13:
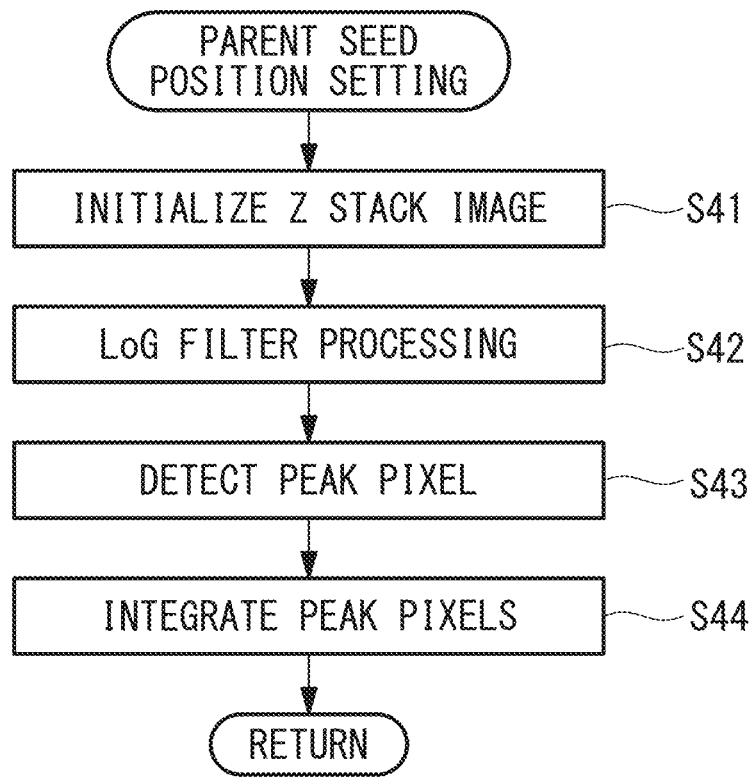
FIG. 13 is a flowchart of a parent seed position setting processing routine in the cell recognition method shown in FIG. 12.

Specifically, as shown in FIG. 13, the Z stack image is initialized by the initializing unit 31 (step S41). Subsequently, LoG filter processing is applied to the Z stack image by the LoG filter unit 32 (step S42). Subsequently, a peak pixel, a LoG filter output value of which indicates a peak, is detected by the peak detecting unit 33 and parent seed information including a coordinate and a pixel value of the peak pixel is created (step S43). Subsequently, peak pixels having sufficiently short distances compared with the average size D among the peak pixels in the parent seed information are integrated by the peak integrating unit 34 (step S44). Positions of the peak pixels remaining after the integration of the peak pixels are set as the parent seed positions P1.

Subsequently, in step S5, a unique identification number is given to each parent seed position P1 in the parent seed information by the first numbering unit 4.

Subsequently, in step S6, the child seed positions P2 are set with respect to each parent seed position P1 in the parent seed information by the second seed-position setting unit 5.

Figure 14:
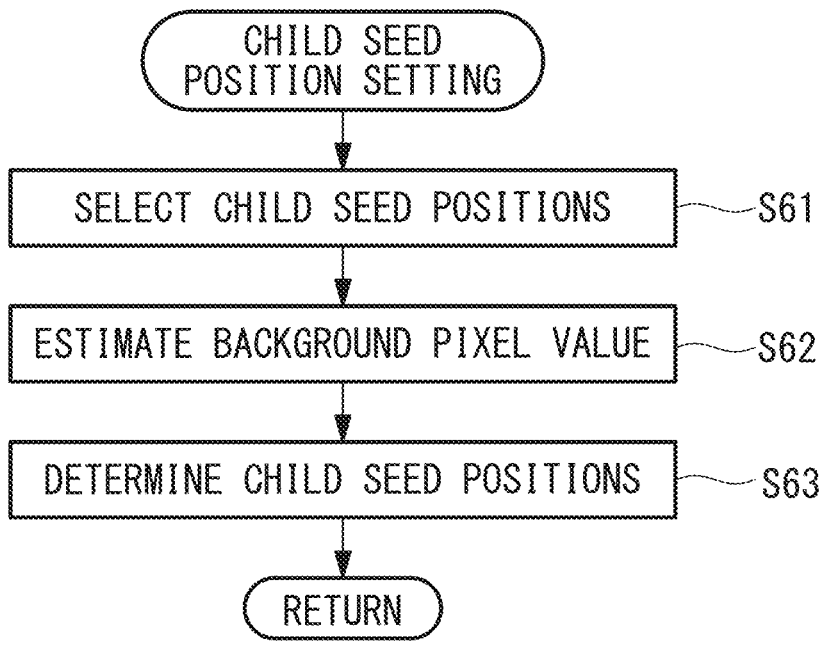
FIG. 14 is a flowchart of a child seed position setting processing routine in the cell recognition method shown in FIG. 12.

Specifically, as shown in FIG. 14, the child seed positions P2 are selected from the range R including each parent seed position P1 in the Z stack image with reference to the parent seed positions P1 in the parent seed information by the child-seed-position selecting unit 51 and child seed information including coordinates and pixel values of the child seed positions P2 is created (step S61). The child seed positions P2 are positions different in the Z direction from the parent seed position P1. Subsequently, a background pixel value of the Z stack image is estimated by the background-value estimating unit 52 (step S62). Subsequently, among the child seed positions P2 selected in step S61, the child seed positions P2, pixel values of which are equal to or smaller than the background pixel value, are deleted from the child seed information by the child-seed-position determining unit 53 (step S63).

Subsequently, in step S7, the same identification number as the identification number of the parent seed position P1 within the same range R, which is a reference source, is given to each child seed position P2 in the child seed information.

Subsequently, in step S8, the parent seed information and the child seed information are integrated into one by the sort unit 7. All seed positions are rearranged in ascending order of distances from the parent seed position P1 of the reference source and sorted seed information is created. In the sorted seed information, the parent seed positions P1 are located in higher order and all the child seed positions P2 are located lower in order than all the parent seed positions P1.

Subsequently, in step S9, a two-dimensional cell region is formed based on the sorted seed information by the cell-region forming unit 8.

Figure 15:
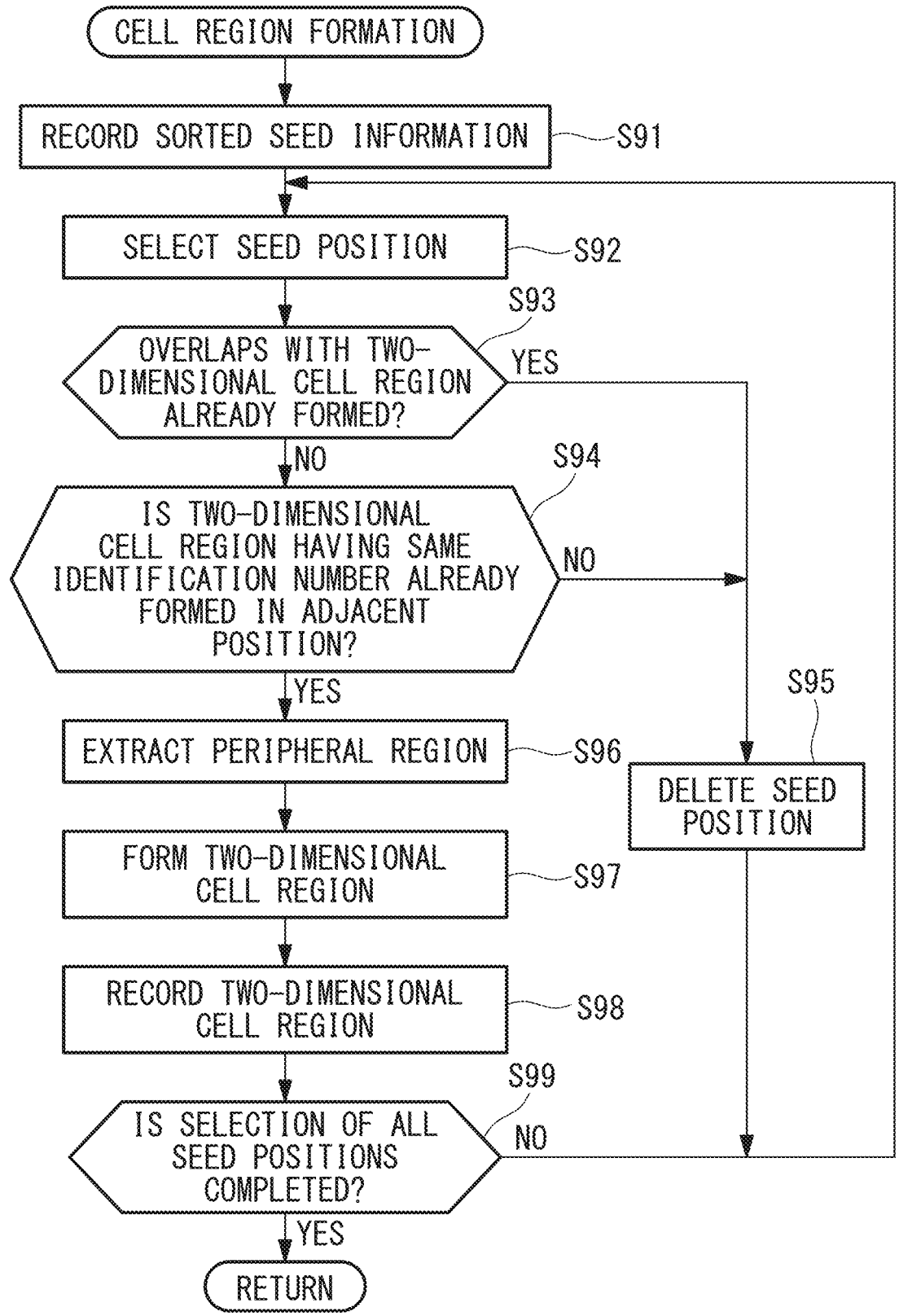
FIG. 15 is a flowchart of a cell region formation processing routine in the cell recognition method shown in FIG. 12.

Specifically, as shown in FIG. 15, the sorted seed information is recorded in the seed recording unit 81 (step S91). Subsequently, the seed positions in the sorted seed information are selected one by one in order from the top by the seed selecting unit 82 (step S92). Subsequently, it is determined by the overlap determining unit 83 whether the selected seed position overlaps the two-dimensional cell region already formed (step S93).

When the selected seed position overlaps the two-dimensional cell region already formed (YES in step S93), the selected seed position is deleted from the sorted seed information recorded in the seed recording unit 81 (step S95). The processing returns to step S92.

On the other hand, when a two-dimensional cell region is not formed in the selected seed position yet (NO in step S93), subsequently, it is determined by the adjacency determining unit 84 whether a two-dimensional cell region having the same identification number is already formed in a position adjacent to the selected seed position in the Z direction (step S94).

When a two-dimensional cell region is not formed in the adjacent position yet or a two-dimensional cell region having a different identification number is already formed (NO in step S94), the selected seed position is deleted from the sorted seed information recorded in the seed recording unit 81 (step S95). The processing returns to step S92.

On the other hand, when a two-dimensional cell region is already formed in the adjacent position and an identification number of the two-dimensional cell region is the same as the identification number of the selected seed position (YES in step S94), subsequently, from a slice image in which the selected seed position is located, a peripheral region centering on the seed position is segmented by the peripheral-region extracting unit 85 and a trimming image is created (step S96).

Subsequently, threshold processing is applied to the trimming image by the two-dimensional-region forming unit 86 and a pixel value of the trimming image is binarized (step S97). Consequently, a two-dimensional cell region is formed in the binarized trimming image. Subsequently, the binarized trimming image including the two-dimensional cell region is recorded in the region recording unit 87 (step S98).

The seed positions in the sorted seed information are selected in order from the top to the bottom by the seed selecting unit 82 (step S99), whereby the processing in steps S93 to S98 is repeatedly executed.

As a result of the execution of step S9, data of a three-dimensional cell region is formed in the region recording unit 87. The data of the three-dimensional cell region is output to a predetermined display device, recording device, or the like from the region recording unit 87 through the output unit 9.

In this case, since the parent seed position P1 is a bright center portion of the cell C, a boundary of the cell C in a trimming image including the parent seed position P1 is accurately recognized by threshold processing. On the other hand, since the child seed position P2 separated from the parent seed position P1 in the Z direction is a dark end portion of the cell C, it is difficult to accurately recognize, with the threshold processing, a boundary of the cell C in a trimming image including the child seed position P2. In this way, recognition accuracy of the cell C in the trimming image in forming a two-dimensional cell region greatly depends on the brightness of the cell C.

In particular, when a plurality of cells C are stereoscopically densely aggregated and in contact with one another as in the spheroid S, it is important to accurately recognize a boundary of adjacent two cells C in order to accurately recognize the individual cells C.

According to this embodiment, two-dimensional cell regions are formed in all the parent seed positions P1 first and thereafter two-dimensional cell regions are formed in the child seed positions P2. Further, two-dimensional cell regions are formed in order from the child seed position P2 at the shortest distance from the parent seed position P1 of the reference source within the same range R. In this way, the two-dimensional cell region is formed first in the bright center portion of the cell C and thereafter the two-dimensional cell region is formed in the dark portion of the cell C. Consequently, it is possible to minimize erroneous recognition of the two-dimensional cell regions and influence on peripheral two-dimensional cell regions by the erroneous recognition. As a result, there is an advantage that it is possible to highly accurately recognize the individual cells C of a cell conglomerate in the stack image and form a three-dimensional cell region accurately representing a three-dimensional region occupied by the individual cells C in the stack image.

Since the cells C in contact with one another affect the shapes of the cells C, the shapes of the cells C in the cell conglomerate are not uniform and are various. According to this embodiment, a three-dimensional cell region is formed from a stacked plurality of two-dimensional cell regions. Each two-dimensional cell region is formed by recognizing the cells C in a slice image. As explained above, the two-dimensional cell regions are formed in all the first seed positions P1 and thereafter the two-dimensional cell regions are formed in order from the second seed position P2 closest to the first seed position P1 of the reference source, whereby the cells C in the slice image are highly accurately recognized. Therefore, there is an advantage that, even if the shapes of the cells C in the stack image are various, it is possible to form a three-dimensional cell region accurately representing the shapes of the individual cells C.

From the above-described embodiment, the following invention is also derived.

A first aspect of the present invention is an image processing device that forms a three-dimensional cell region from a stack image obtained by photographing a plurality of cells, the stack image being configured from a plurality of two-dimensional slice images stacked in a stack direction, the three-dimensional cell region being formed by stacking a plurality of two-dimensional cell regions, the image processing device including: a first seed-position setting unit that sets a plurality of first seed positions in the stack image, each of the plurality of first seed positions being a position of a pixel, a pixel value of which indicates a three-dimensional peak; a first numbering unit that gives a unique identification number to each of the plurality of first seed positions; a standard-size setting unit that sets a standard size of a cell in a predetermined direction of the stack image; a second seed-position setting unit that sets, referring to each of the plurality of first seed positions, second seed positions within a range of the standard size centering on each of the plurality of first seed positions, the second seed positions being positions shifted in the predetermined direction with respect to the first seed positions; a second numbering unit that gives an identification number to each of the second seed positions, the identification number of each of the second seed positions being same as the identification number of the first seed position referred to in the setting of the second seed positions; and a cell-region forming unit that forms a two-dimensional cell region in each of the first and second seed positions, the two-dimensional cell region being a region crossing the predetermined direction, wherein the cell-region forming unit forms the two-dimensional cell regions in each of all the first seed positions and thereafter forms the two-dimensional cell regions in each of the second seed positions.

According to this aspect, the position where the pixel value indicates the peak in the stack image is set as the first seed position by the first seed-position setting unit. The identification number is given to each first seed position by the first numbering unit. The center portion of the cell in the stack image usually indicates the peak of the pixel value. Therefore, the first seed positions are set in the center portions of the individual cells in the stack image.

Subsequently, the second seed positions are set within the range centering on each first seed position by the second seed-position setting unit with reference to each first seed position. A size of the range is a standard size of the cell set by the standard-size setting unit. Therefore, the second seed positions are set within a range occupied by the individual cells in the stack image. Subsequently, the same identification number as the identification number of the first seed position, which is a reference source, is given to each second seed position by the second numbering unit. Subsequently, the two-dimensional cell region is formed in the each of first and second seed positions by the cell-region forming unit. Consequently, the three-dimensional cell region is formed from the plurality of two-dimensional cell regions stacked in the predetermined direction.

In this case, in the image, the center portion of the cell is the brightest and brightness decreases from the center portion of the cell toward a peripheral portion of the cell. Therefore, it is possible to accurately recognize a region shape of the center portion of the cell compared with the peripheral portion of the cell. The cell-region forming unit forms the two-dimensional cell regions in all the first seed positions and thereafter forms the two-dimensional cell regions in the second seed positions. Therefore, even if cells are crowded, the individual cell regions are accurately recognized. Consequently, it is possible to highly accurately recognize the individual cells in the image of the cell conglomerate.

In the first aspect, the two-dimensional cell region may be formed on a plane perpendicularly crossing the stack direction.

With this configuration, it is possible to form the two-dimensional cell region on the slice image or on a plane parallel to the slice image.

In the first aspect, the predetermined direction may be the stack direction.

With this configuration, it is possible to form the individual three-dimensional cell regions from the two-dimensional cell regions stacked in the stack direction.

In the first aspect, the image processing device may include an average-size setting unit that sets an average size of the cells on a plane crossing the stack direction. The standard-size setting unit may set the standard size based on the average size.

An image of the cell apparently sometimes extends in the stack direction because of optical blur or the like. In such a case, it is possible to set a more appropriate standard size considering extension of a size of the cell in the predetermined direction.

In the first aspect, the image processing device may include a feature-value calculating unit that calculates a feature value of each pixel in the stack image, the feature value being an amount representing likelihood of a pixel value being an extreme value. The first seed-position setting unit may set a position of a pixel having the feature value larger than the feature value of a peripheral pixel as the first seed position.

Since the center portion of the cell is brighter than the periphery of the cell, a feature value of a pixel in the center portion of the cell is larger than a feature value of a peripheral pixel. Therefore, it is possible to detect, based on the feature value, the center portion of the cell where the first seed position should be set.

In the first aspect, the feature value may be a LoG filter output value.

With this configuration, it is possible to calculate the LoG filter output value as a feature value that accurately represents likelihood of a pixel value being an extreme value.

In the first aspect, the cell-region forming unit may define a boundary of the two-dimensional cell region based on at least one of a pixel value distribution and a pixel value gradient around each of the first and second seed positions.

In a boundary of a cell, a pixel value and a pixel value gradient are large compared with the periphery of the cell. Therefore, it is possible to highly accurately recognize a boundary of the cell in the stack image based on at least one of a pixel value distribution and a pixel value gradient and define the detected boundary as a boundary of the two-dimensional cell region.

In the first aspect, the cell-region forming unit may define the boundary with adaptive threshold processing of at least one of the pixel value distribution and the pixel value gradient.

With this configuration, it is possible to more highly accurately recognize the boundary of the cell in the stack image.

In the first aspect, only when a two-dimensional cell region having a same identification number as the identification number of the second seed position is already formed in the first seed position or another one of the second seed positions adjacent to the second seed position in the predetermined direction, the cell-region forming unit may form the two-dimensional cell region in the second seed position.

With this configuration, only when the two-dimensional cell region having the same identification number is already formed adjacent to the second seed position, the two-dimensional cell region is formed in the second seed position. Consequently, it is possible to form a three-dimensional cell region continuous in a predetermined direction.

In the first aspect, the cell-region forming unit may form the two-dimensional cell regions in order from the second seed position at a smallest distance from the first seed position, which is a reference source.

With this configuration, after the two-dimensional cell region is formed in the first seed position in the center portion of the cell, the two-dimensional cell regions are formed in order from a near side to the center portion of the cell toward a far side. Consequently, it is possible to form the two-dimensional cell regions in order from a brightest position and more highly accurately recognize the individual cells.

In the first aspect, the second seed-position setting unit may select, as a candidate of the second seed position, a position shifted in the predetermined direction with respect to the first seed position and, only when a pixel value in the selected position is larger than a predetermined value, set the selected position as the second seed position.

Besides the cell, a background can be included within a range of a standard size centering on the first seed position. The pixel value in the cell is higher than the pixel value in the background. Therefore, by comparing the pixel value of the position selected as the candidate of the second seed position with the predetermined value, it is possible to determine whether the selected position is a position in the cell or a position in the background. By setting only the position determined as the position in the cell as the second seed position, it is possible to prevent the two-dimensional cell region from being formed by mistake in the background in the stack image.

In the first aspect, the image processing device may include a background-value estimating unit that estimates an average pixel value of a background region in the stack image, the background region being a region not including the cell, and the predetermined value may be set based on the average pixel value of the background region.

With this configuration, it is possible to accurately determine whether the position selected as the candidate of the second seed position is a position in the cell or a position in the background.

A second aspect of the present invention is a cell recognition apparatus including: an imaging unit that acquires a stack image obtained by photographing a plurality of cells; and the image processing device described in any one of the paragraphs described above.

A third aspect of the present invention is a cell recognition method for forming a three-dimensional cell region from a stack image obtained by photographing a plurality of cells, the stack image being configured from a plurality of two-dimensional slice images stacked in a stack direction, the three-dimensional cell region being formed by stacking a plurality of two-dimensional cell regions, the image recognition method including: a step of setting a plurality of first seed positions in the stack image, each of the plurality of first seed positions being a position of a pixel, a pixel value of which indicates a three-dimensional peak; a step of giving a unique identification number to each of the plurality of first seed positions; a step of setting a standard size of a cell in a predetermined direction of the stack image; a step of setting, referring to each of the plurality of first seed positions, second seed positions within a range of the standard size centering on each of the plurality of first seed positions, the second seed positions being positions shifted in the predetermined direction with respect to the first seed positions; a step of giving an identification number to each of the second seed positions, the identification number of each of the second seed positions being same as the identification number of the first seed position referred to in the setting of the second seed positions; and a step of forming a two-dimensional cell region in each of the first and second seed positions, the two-dimensional cell region being a region crossing the predetermined direction, wherein, in the step of forming the two-dimensional cell region, the two-dimensional cell region is formed in each of all the first seed positions and thereafter the two-dimensional cell region is formed in each of the second seed positions.

A fourth aspect of the present invention is a cell recognition program for causing a processor to execute processing for forming a three-dimensional cell region from a stack image obtained by photographing a plurality of cells, the stack image being configured from a plurality of two-dimensional slice images stacked in a stack direction, the three-dimensional cell region being formed by stacking a plurality of two-dimensional cell regions, the cell recognition program causing the processor to execute: a step of setting a plurality of first seed positions in the stack image, each of the plurality of first seed positions being a position of a pixel, a pixel value of which indicates a three-dimensional peak; a step of giving a unique identification number to each of the plurality of first seed positions; a step of setting a standard size of a cell in a predetermined direction of the stack image; a step of setting, referring to each of the plurality of first seed positions, second seed positions within a range of the standard size centering on each of the plurality of first seed positions, the second seed positions being positions shifted in the predetermined direction with respect to the first seed positions; a step of giving an identification number to each of the second seed positions, the identification number of each of the second seed positions being same as the identification number of the first seed position referred to in the setting of the second seed positions; and a step of forming a two-dimensional cell region in each of the first and second seed positions, the two-dimensional cell region being a region crossing the predetermined direction, wherein, in the step of forming the two-dimensional cell region, the two-dimensional cell region is formed in each of all the first seed positions and thereafter the two-dimensional cell region is formed in each of the second seed positions.

REFERENCE SIGNS LIST 1 average-size setting unit
2 standard-size setting unit
3 first seed-position setting unit
4 first numbering unit
5 second seed-position setting unit
6 second numbering unit
7 sort unit
8 cell-region forming unit
9 output unit
10 image processing device
20 imaging device (imaging unit)
100 cell recognition apparatus
D average size
D' standard size
P1 parent seed position (first seed position)
P2 child seed position (second seed position)

The invention claimed is:

1. An image processing device that forms a three-dimensional cell region from a stack image obtained by photographing a plurality of cells, the stack image being configured from a plurality of two-dimensional slice images stacked in a stack direction, the three-dimensional cell region being formed by stacking a plurality of two-dimensional cell regions, and the image processing device comprising a processor comprising hardware configured to:
set a plurality of first seed positions in the stack image, each of the plurality of first seed positions being a position of a pixel, a pixel value of which indicates a three-dimensional peak;
give a unique identification number to each of the plurality of first seed positions;
set a standard size of a cell in a predetermined direction of the stack image;
set, with respect to each of the plurality of first seed positions, second seed positions within a range of the standard size centering on the first seed position, the second seed positions being positions shifted in the predetermined direction with respect to the first seed position;
give an identification number to each of the second seed positions, the identification number of each of the second seed positions being the same as the identification number of the first seed position with respect to which the second seed positions were set; and
form a two-dimensional cell region in each of the first and second seed positions, the two-dimensional cell region being a region crossing the predetermined direction,
wherein:
in the forming of the two-dimensional cell region, the processor is configured to select each of the first seed positions and each of the second seed positions, and to form the two-dimensional cell region in each of the first seed positions and each of the second seed positions in order of selection, and
in the selecting of each of the first seed positions and each of the second seed positions, the processor is configured to select the second seed positions after all of the first seed positions have been selected.

2. The image processing device according to claim 1, wherein the processor is configured to form the two-dimensional cell region in each of the first seed positions and each of the second seed positions on planes perpendicularly crossing the stack direction.

3. The image processing device according to claim 1, wherein the predetermined direction is the stack direction.

4. The image processing device according to claim 3, wherein the processor is configured to:
set an average size of the cells on a plane crossing the stack direction; and
set the standard size based on the average size.

5. The image processing device according to claim 1, wherein the processor is configured to:
calculate a feature value of each pixel in the stack image, the feature value being an amount representing a likelihood of a pixel value being an extreme value; and
set a position of a pixel whose feature value is larger than the feature value of a peripheral pixel as the first seed position.

6. The image processing device according to claim 5, wherein the feature value is a LoG filter output value.

7. The image processing device according to claim 1, wherein the processor is configured to define a boundary of the two-dimensional cell region based on at least one of a pixel value distribution and a pixel value gradient around each of the first and second seed positions.

8. The image processing device according to claim 7, wherein the processor is configured to define the boundary with adaptive threshold processing of at least one of the pixel value distribution and the pixel value gradient.

9. The image processing device according to claim 1, wherein, only when a two-dimensional cell region having a same identification number as the identification number of a respective one of the second seed positions to be formed is already formed in the first seed position or another one of the second seed positions adjacent to the respective one of the second seed positions in the predetermined direction, the processor is configured to form the two-dimensional cell region in the respective one of the second seed positions.

10. The image processing device according to claim 1, wherein the processor is configured to select the second seed positions in order from the second seed position at a smallest distance from the first seed position, which is a reference source, and to form the two-dimensional cell regions in the second seed positions in order of selection.

11. The image processing device according to claim 10, wherein in the forming the two-dimensional cell regions, a two-dimensional cell region to be formed in a respective one of the selected second seed positions is not formed in a case in which a two-dimensional cell region is not already formed at a position which is adjacent to the respective one of the selected second seed positions and closer to the first seed position than the respective one of the selected second seed positions.

12. The image processing device according to claim 1, wherein the processor is configured to:
select, as a candidate of the second seed position, a position shifted in the predetermined direction with respect to the first seed position, and determine whether or not a pixel value in the selected position is larger than a predetermined value;
in response to determining that the pixel value in the selected position is larger than the predetermined value, set the selected position as the second seed position; and
in response to determining that the pixel value in the selected position is not larger than the predetermined value, not set the selected position as the second seed position.

13. The image processing device according to claim 12, wherein:
the processor is configured to estimate an average pixel value of a background region in the stack image, the background region being a region not including the cells, and
the predetermined value is set based on the average pixel value of the background region.

14. The image processing device according to claim 1, further comprising at least one interface coupled to an image sensor that acquires a stack image obtained by photographing a plurality of cells, the image processing device and the image sensor being included in a cell recognition apparatus.

15. The image processing device according to claim 1, wherein the three-dimensional cell region is formed by stacking the two-dimensional cell regions formed in each of the first seed positions and the two-dimensional cell regions formed in each of the second seed positions.

16. The image processing device according to claim 1, wherein in the forming of the two-dimensional cell region, the processor is configured to form the two-dimensional cell region in all of the first seed positions and, after forming the two-dimensional cell region in all of the first seed positions, form the two-dimensional cell region in each of the second seed positions.

17. The image processing device according to claim 1, wherein the processor is configured to:
select one of the second seed positions and determine whether the selected second seed position satisfies a predetermined condition, the predetermined condition being a condition that a two-dimensional cell region having a same identification number as the identification number of the selected second seed position is already formed in the first seed position adjacent to the selected second seed position in the predetermined direction or another one of the second seed positions adjacent to the selected second seed position in the predetermined direction;
in response to determining that the selected second seed position satisfies the predetermined condition, forming the two-dimensional cell region in the selected second seed position; and
in response to determining that the selected second seed position does not satisfy the predetermined condition, not forming the two-dimensional cell region in the selected second seed position.

18. The image processing device according to claim 1, wherein the processor is configured to:
rearrange the second seed positions in order from the second seed position at a smallest distance from the first seed position, which is a reference source;
select the second seed positions in the order in which they have been rearranged; and
form the two-dimensional cell regions in order of selection.

19. A cell recognition method for forming a three-dimensional cell region from a stack image obtained by photographing a plurality of cells, the stack image being configured from a plurality of two-dimensional slice images stacked in a stack direction, the three-dimensional cell region being formed by stacking a plurality of two-dimensional cell regions, and the image recognition method comprising:
setting a plurality of first seed positions in the stack image, each of the plurality of first seed positions being a position of a pixel, a pixel value of which indicates a three-dimensional peak;
giving a unique identification number to each of the plurality of first seed positions;
setting a standard size of a cell in a predetermined direction of the stack image;
setting, with respect to each of the plurality of first seed positions, second seed positions within a range of the standard size centering on the first seed position, the second seed positions being positions shifted in the predetermined direction with respect to the first seed position;
giving an identification number to each of the second seed positions, the identification number of each of the second seed positions being the same as the identification number of the first seed position with respect to which the second seed positions were set; and
forming a two-dimensional cell region in each of the first and second seed positions, the two-dimensional cell region being a region crossing the predetermined direction,
wherein:
the forming of the two-dimensional cell region comprises selecting each of the first seed positions and each of the second seed positions, and forming the two-dimensional cell region in each of the first seed positions and each of the second seed positions in order of selection, and in the selecting of each of the first seed positions and each of the second seed positions, the second seed positions are selected after all of the first seed positions have been selected.

20. A non-transitory computer-readable medium having a cell recognition program stored therein, the cell recognition program causing a processor to execute processing for forming a three-dimensional cell region from a stack image obtained by photographing a plurality of cells, the stack image being configured from a plurality of two-dimensional slice images stacked in a stack direction, the three-dimensional cell region being formed by stacking a plurality of two-dimensional cell regions, and the cell recognition program causing the processor to execute functions comprising:

setting a plurality of first seed positions in the stack image, each of the plurality of first seed positions being a position of a pixel, a pixel value of which indicates a three-dimensional peak;

giving a unique identification number to each of the plurality of first seed positions;

setting a standard size of a cell in a predetermined direction of the stack image;

setting, with respect to each of the plurality of first seed positions, second seed positions within a range of the standard size centering on the first seed position, the second seed positions being positions shifted in the predetermined direction with respect to the first seed position;

giving an identification number to each of the second seed positions, the identification number of each of the second seed positions being the same as the identification number of the first seed position with respect to which the second seed positions were set; and forming a two-dimensional cell region in each of the first and second seed positions, the two-dimensional cell region being a region crossing the predetermined direction, wherein:

the forming of the two-dimensional cell region comprises selecting each of the first seed positions and each of the second seed positions, and forming the two-dimensional cell region in each of the first seed positions and each of the second seed positions in order of selection, and in the selecting of each of the first seed positions and each of the second seed positions, the second seed positions are selected after all of the first seed positions have been selected.

* * * * *